(12) United States Patent
Parravicini

(10) Patent No.: US 8,684,906 B2
(45) Date of Patent: Apr. 1, 2014

(54) CARDIOVASCULAR DEVICE

(76) Inventor: Roberto Parravicini, Modena (IT)

( * ) Notice: Subject to any disclaimer, the term of this patent is extended or adjusted under 35 U.S.C. 154(b) by 0 days.

(21) Appl. No.: 13/702,364

(22) PCT Filed: Jun. 7, 2011

(86) PCT No.: PCT/IB2011/052470
§ 371 (c)(1),
(2), (4) Date: Dec. 6, 2012

(87) PCT Pub. No.: WO2011/154892
PCT Pub. Date: Dec. 15, 2011

(65) Prior Publication Data
US 2013/0079583 A1    Mar. 28, 2013

(30) Foreign Application Priority Data

Jun. 8, 2010 (IT) .............................. MO2010A0166

(51) Int. Cl.
*A61M 1/12* (2006.01)
(52) U.S. Cl.
USPC ............................................ 600/18; 623/3.1

(58) Field of Classification Search
USPC ............................................... 600/18; 623/3.1
See application file for complete search history.

(56) References Cited

U.S. PATENT DOCUMENTS 5,139,517 A * 8/1992 Corral ............................ 623/3.1
2007/0161846 A1 7/2007 Nikolic

* cited by examiner

*Primary Examiner* — Christopher D Koharski
*Assistant Examiner* — Michael Carey
(74) *Attorney, Agent, or Firm* — R. Neil Sudol; Henry D. Coleman

(57) ABSTRACT

A cardiovascular device (11), adapted to be fitted into a cardiac ventricular cavity (2) having a volume with blood flowing therethrough, which is bounded by walls (8) and has a larger longitudinal dimension (D1) and a smaller transverse dimension (D2). The device includes a diaphragm (16) that can be disposed in the ventricular cavity (2) substantially transverse to the larger longitudinal dimension (D1), in such an arrangement as to reduce ventricular volume, the diaphragm (16) having a peripheral edge (15) which can be sealingly engaged with the ventricle walls (8) and being adapted to be alternately driven between an active blood pushing displacement and an inactive return displacement.

12 Claims, 4 Drawing Sheets

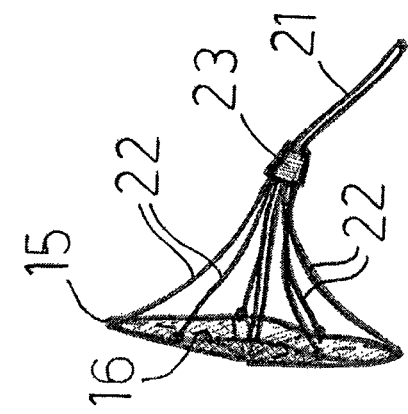
FIG. 7
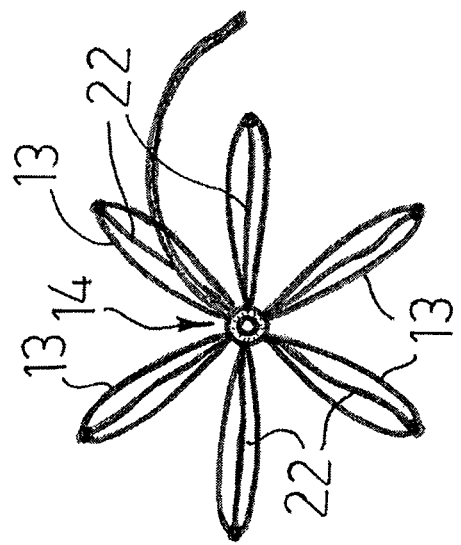
FIG. 5
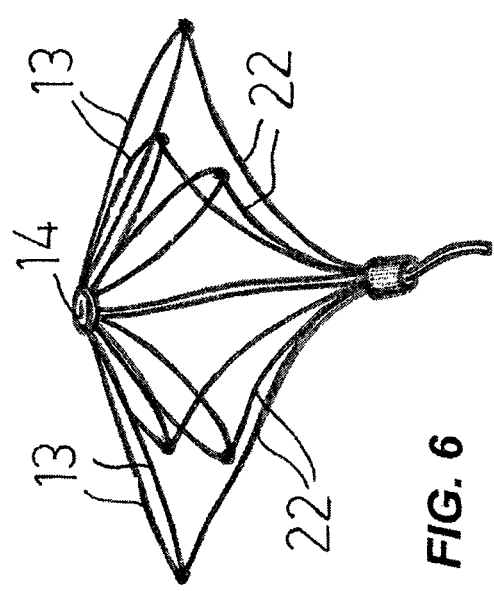
FIG. 4
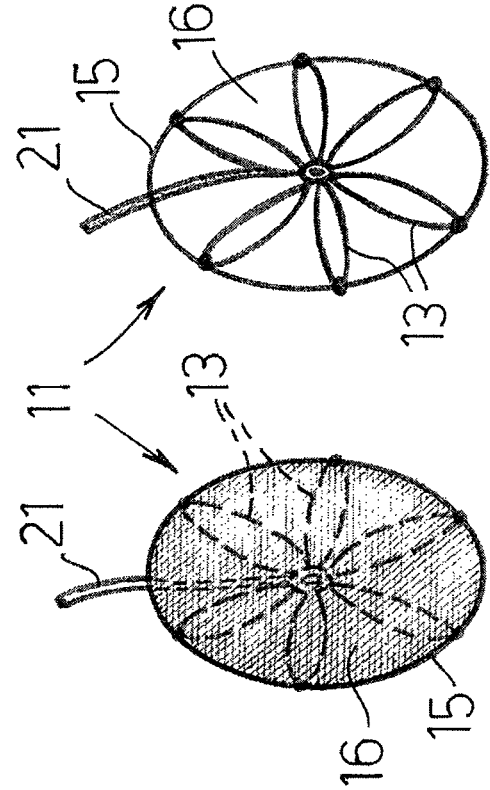
FIG. 6
FIG. 3

CARDIOVASCULAR DEVICE

The present application is the U.S. national stage of International Patent Application No. PCT/IB2011/052470 filed 7 Jun. 2011 and claims priority under 35 U.S.C. §119 to Italian Patent Application Number MO2010A000166 filed 8 Jun. 2010.

FIELD OF THE INVENTION

The invention relates to a cardiovascular device which is namely adapted to obviate the problems caused by heart failure, i.e. caused by heart-dilating diseases.

BACKGROUND ART

Heart failure is currently the most serious cardiovascular disease affecting heart patients and may be caused, for instance, by a cardiac muscle dilating disease.

This disease causes an enlargement of the heart cavity, particularly the ventricles and especially the left ventricle which is the mostly stressed to pump blood into the blood circuit of living beings.

Such enlargement of the left ventricle causes a blood pressure drop and hence dangerously reduces blood supply to vital organs, such as lungs, brain and kidneys.

Two remedies have been used heretofore to treat this disease: the first remedy consists in subjecting the patient to heart transplantation surgery and the second remedy consist in connecting the patient to an auxiliary, portable pump apparatus.

The above described prior art suffers from certain drawbacks.

A first drawback concerning transplantation is that it is not always easy to find a donor that can provide an organ for transplantation and that the death of the donor is always implied.

Furthermore, after transplantation surgery, the patient is required to undergo long treatment to avoid or reduce any rejection of the transplanted heart by his/her organism.

Another drawback, concerning the use of an auxiliary pump apparatus, consists in that the latter has to be carried by the patient during the day and, since this auxiliary pump apparatus also requires the use of a battery pack for operation, the whole shall be put in a case and connected to the patient by tubes that come out of the case and reach special connectors implanted beforehand in the patient's body.

Therefore, in both cases life quality is strongly affected and the patient is considerably limited in the performance of daily activities.

DISCLOSURE OF THE INVENTION

It is an object of the present invention to improve the prior art.

Another object of the invention is to provide a cardiovascular device that can quickly remedy heart failure caused by a heart dilating disease.

Yet another object of the invention is to provide a cardiovascular device that can be stably fitted on site by a surgical procedure that substantially remedies the heart disease.

A further object of the invention is to provide a cardiovascular device that, after transplantation, allows the patient to have a substantially normal life, and avoids the need of carrying auxiliary devices, without resorting to heart transplantation.

In one aspect, the invention provides a cardiovascular device as defined in claim 1.

BRIEF DESCRIPTION OF THE DRAWINGS

Further features and advantages of the invention will be more readily apparent upon reading of the detailed description of a preferred non-exclusive embodiment of a cardiovascular device, which is shown by way of illustration and without limitation by the annexed drawings, in which:

FIG. 3 is a front view of the cardiovascular device of the invention;

FIG. 4 is a corresponding rear view of the cardiovascular device of FIG. 3;

FIG. 5 is a corresponding side view of the cardiovascular device of FIG. 3;

FIG. 6 is a side view of a frame which is part of the cardiovascular device of the invention;

FIG. 7 is a corresponding front view of the frame of FIG. 6;

DETAILED DESCRIPTION OF ONE PREFERRED EMBODIMENT

Figure 1:
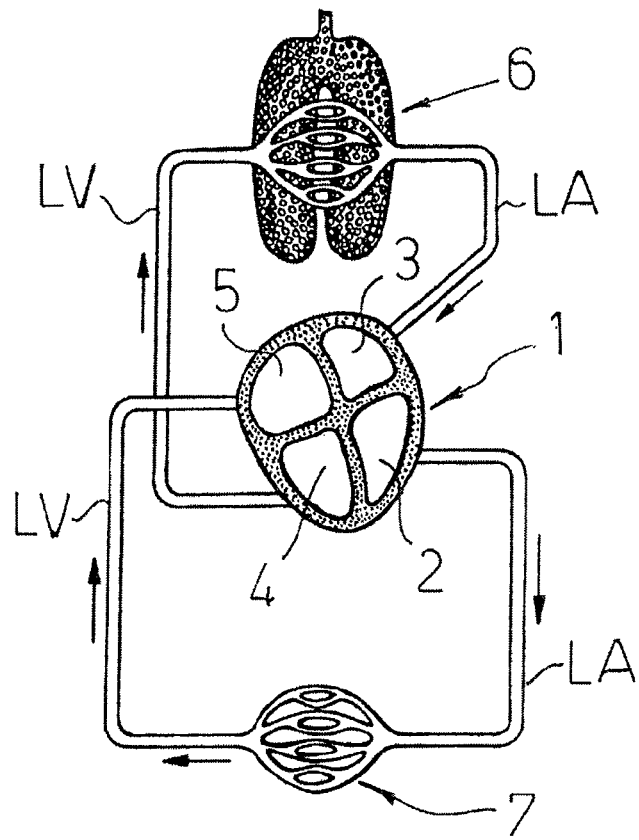
FIG. 1 is a highly schematic view of the cardiovascular system of a living being.

Referring to FIG. 1, numeral 1 designates a heart, numeral 2 a left ventricle, numeral 3 a left atrium, numeral 4 a right ventricle and numeral 5 a right atrium of the heart 1.

"LA" designates an arterial blood line and "LV" a venous line, whereas numeral 6 designates the lungs and numeral 7 the scheme of the whole peripheral vascular system.

Figure 2:
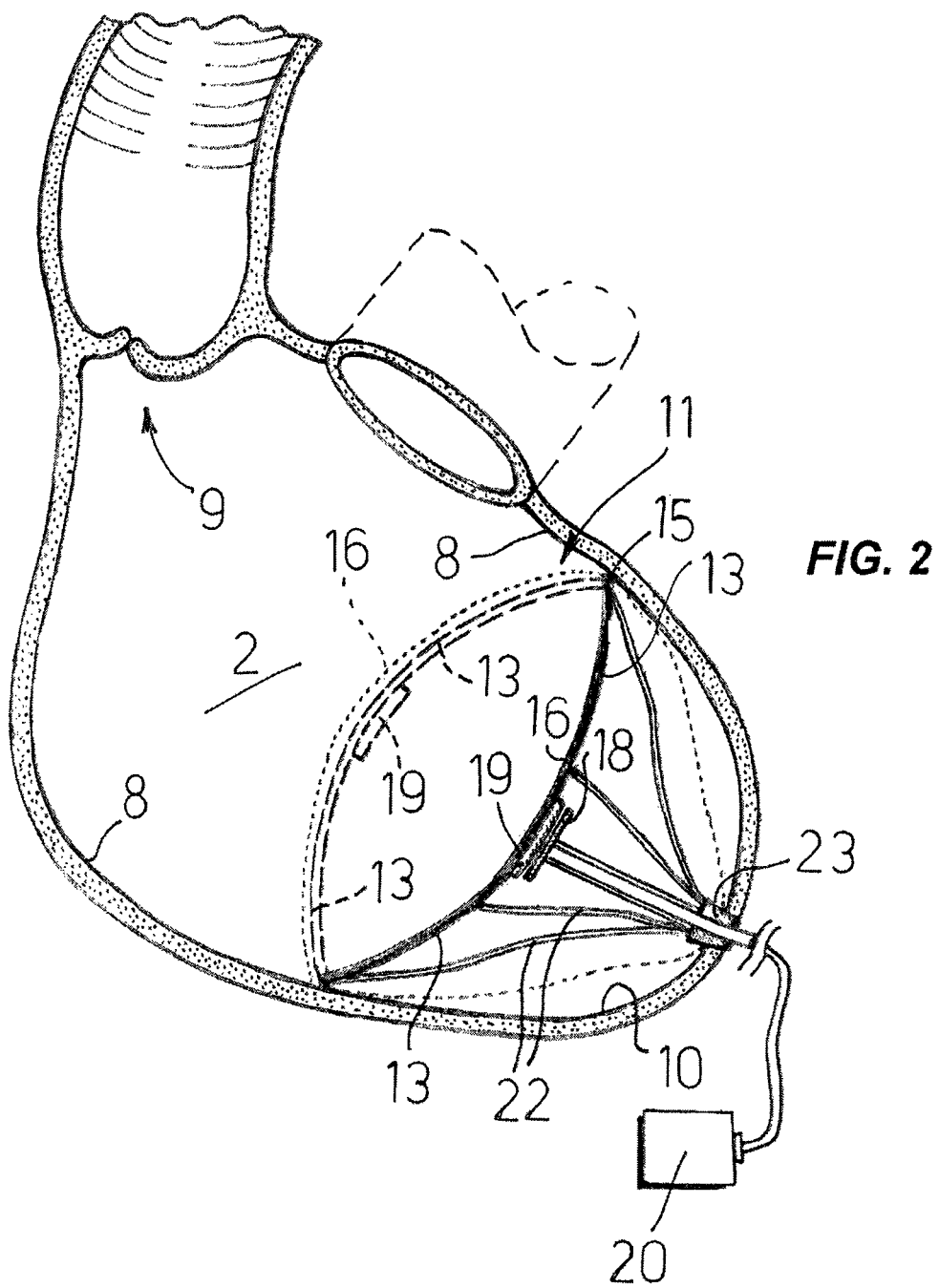
FIG. 2 is a schematic and greatly enlarged view of the left ventricle of a heart in which a cardiovascular device of the invention has been placed.

Referring to FIG. 2, the left ventricle 2 is shown to have peripheral walls 8 that delimit it and to have an elongate shape, in which a larger dimension "D1" is defined, extending from the aortic valve 9 to the blind end 10 of the ventricle.

The smaller dimension "D2" is the transverse dimension, and a cardiovascular device 11 of the invention is designed to be fitted between the opposed walls that delimit it.

Referring to FIGS. 3 to 7, a first embodiment of the cardiovascular device is shown to comprise a rectangular frame 12 composed of a plurality of radially arranged arms 13 which have converging ends ending up into a first central hub 14 with which they are hinged, and opposite ends that are hinged to a peripheral edge 15 which is designed to abut against and sealingly engage the walls of the ventricle 2, in which it can be typically integrated with time.

The cardiovascular device 11 has such an overall transverse dimension as to be fitted transverse to the larger dimension "D1" of the ventricle 1, thereby partially reducing the overall internal volume thereof.

A flexible sheet element 16, namely a diaphragm, stretching from the peripheral edge 15 and supported by the arms 13, is attached to the frame 12.

As better shown in FIG. 2, in an alternative embodiment of a vascular device 11, a telescopic guide stem 17 is provided, which can be adjusted in length, and has a first end facing towards the hub 14 that supports a first magnetic element, e.g.

an electromagnet 18, whereas a second magnetic element, also an electromagnet 19, is supported by the hub 14.

At least the electromagnet 18 is connected to an electric generator 20, such as a battery pack, which supplies AC current thereto, to provide alternate and cyclic attractive and repulsive forces between the two electromagnets 18 and 19.

Referring to FIGS. 3 to 7, the cardiovascular device 11 is shown to have a slightly simplified structure, with no guide stem 17, the latter being replaced by a cord 21 which is configured to be attached to the blind end 10 of the vascular cavity 2.

The arms 13 have respective support elements 22 with respective ends hinged to the peripheral edge 15 and opposed converging ends, hinged to a second hub 23, which is designed to be integrated with the end 10 of the vascular cavity 2, so that the vascular device 11 may be stably arranged therein.

In order to protect the integrity of its parts of from any degradation caused by use, the cardiovascular device 11 is placed in a protective sheath, outlined by the broken line 24 of FIG. 2, which wraps it entirely in a loose manner, to allow for pushing and return movement.

The operation of the vascular device 11 is described below separately for the two possible embodiments.

In the embodiment as shown in FIGS. 3 to 7, i.e. the one with no guide stem 17, the vascular device 11 is introduced by surgery into the vascular cavity 2, transverse to the larger dimension "D1" thereof, with the peripheral edge 15 abutting and slightly pressing against the walls 8, to create a seal therewith.

Thus, the cardiovascular device 11 divides the cavity 2 into two portions, which have smaller volumes than the overall volume of the cavity 2, one of which portions is only designed to receive blood therein, namely the one facing towards the aortic valve 9.

Figure 8:
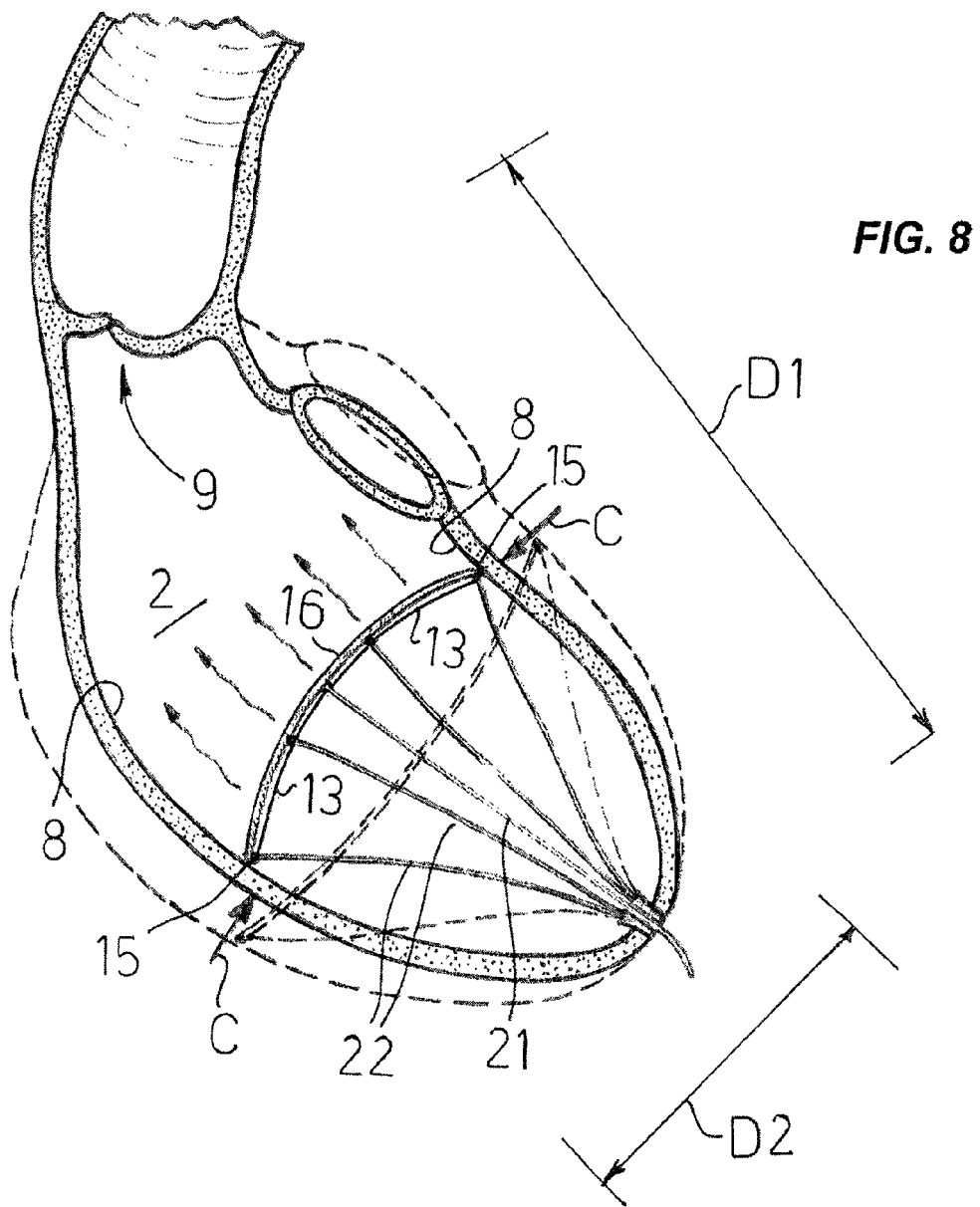
FIG. 8 is a highly schematic view of a heart ventricle in which the vascular device of the invention has been inserted and in a possible embodiment, as also shown in FIGS. 3 to 7, during heart systole.

In order to add stability to the cardiovascular device 11, the surgeon forms a passage in the blind cavity 10 for insertion of the second hub 23, through which the cord 21 also passes, as shown in FIG. 8.

Thus, the vascular device 11 is firmly fitted in the vascular cavity 2, as it is secured both by the edge 15 against the walls 8 and by the second hub 23 in the blind end 10.

When the vascular cavity 2 contracts during heart systole, the walls 8 press the frame 12 in a centripetal direction, as schematically shown by the arrows "C" of FIG. 8 and the arms 13 (as well as the peripheral edge 15) bend or deform, as they are made of a flexible, shape-memory material, thereby turning inside out the diaphragm 16 towards the aortic valve 9 and hence providing a further blood pushing action, in addition to the one provided by systolic contraction of the vascular cavity 2.

As soon as the compressive action of the systole stops, the arms 13 revert to their normal conformation.

Figure 9:
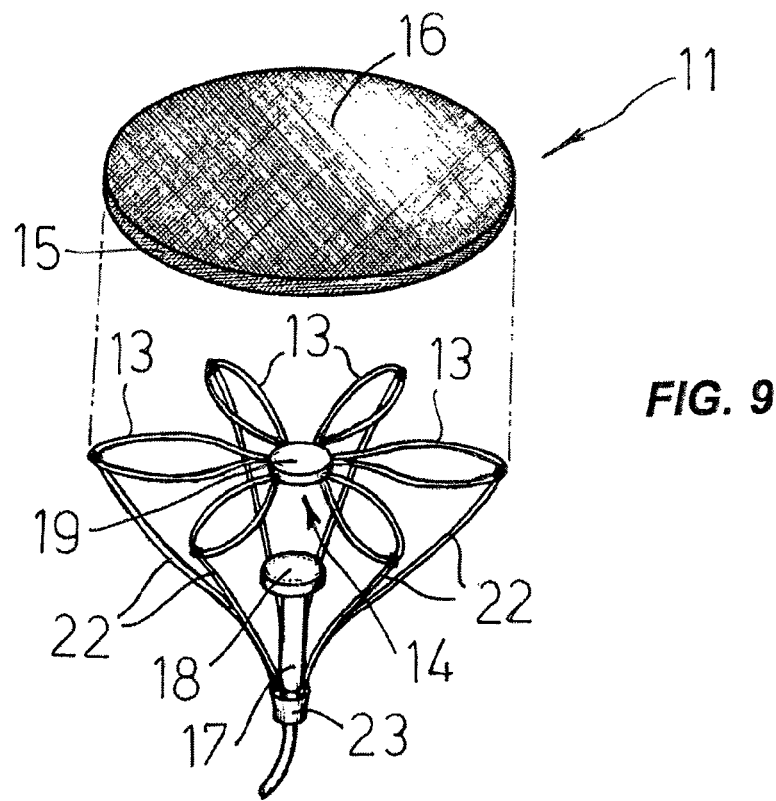
FIG. 9 is a highly schematic exploded view of an alternative embodiment of a cardiovascular device of the invention.

In the second embodiment of the vascular device 11, as shown in FIGS. 2 and 9, the position of the latter in the cavity 2 is shown to be substantially as described above.

The difference between the two embodiments of the vascular device 11 is that the two electromagnets 18 and 19 are caused to alternately attract or repel by changing the polarity of at least one of them.

These cyclic attractions and repulsions cause the diaphragm 16 to be turned in or out, thereby providing a pumping effect that, as described above, is added to the pumping effect generated by the systole in the vascular cavity 2.

Cyclic polarity reversal of one of the electromagnets 18 or 19 may be obtained by providing an electric AC generator 20, such as a battery pack, which is mounted outside the heart, like in pacemaker devices, and is connected to the vascular device 11 by means of a power cable that the surgeon passes through the blind end 10 during placement of the vascular device 11.

Nevertheless, in both embodiments, the result is that the vascular cavity 2 is divided by the device into two portions having smaller volumes than the overall volume of the vascular cavity 2, thereby improving the blood pushing capacity.

This is supplemented by the effect of the in-and out-turning diaphragm 16, which considerably increases the pushing force, thereby improving blood supply to the peripheral vascular system 7.

The invention has been found to fulfill the intended objects.

The invention so conceived is susceptible to changes and variants within the inventive concept.

Also, all the details may be replaced by other technical equivalent elements. In practice, any material, shape and size may be used as needed, without departure from the scope as defined by the following claims.

The invention claimed is:

1. A cardiovascular device, to be fitted in a ventricular cardiac cavity having a volume wherein blood flows, which is bounded by walls and has a greater longitudinal dimension and a smaller transverse dimension, said device comprising a diaphragm assembly that can be fitted inside said ventricular cardiac cavity substantially transverse to said greater longitudinal dimension, so as to reduce said volume, said diaphragm assembly having a peripheral edge which can be sealingly engaged with said walls and being alternatively driven between an active shifting of pushing blood and an inactive back shifting, said diaphragm assembly including said peripheral edge being deformable at least partially in response to contraction of said walls.

2. A device according to claim 1, wherein each of said active shifting and inactive shifting are substantially synchronized respectively with a systole and a diastole of the heart.

3. A device according to claim 1, wherein said diaphragm assembly is movably actuated in substantial part by an actuator.

4. A device according to claim 1, wherein said diaphragm assembly is movably driven at least principally by pushes of said walls during systole and diastole.

5. A device according to claim 3, wherein said diaphragm assembly comprises: a planar element equipped with said peripheral edge, movable alternatively between a pushing position and a backward position; and a support frame of said planar element that is movable between said pushing position and backward position together with said planar element.

6. A device according to claim 5, wherein said frame comprises a substantially rectilinear guiding element that has an adjustable length and defines a first end facing said planar element and an opposite second end facing a blind end of said cardiac cavity and associable to the latter.

7. A device according to claim 6 wherein said actuator comprises a couple of magnetic bodies, a first body of which is mounted on said support frame and a second body of which is mounted on said first end of said guiding element, and fed by an electric circuit and designed to attract and repel each other alternatively so as to perform said active and inactive movements.

8. A device according to claim 5, wherein said planar element comprises a laminar flexible diaphragm made of a bio-compatible material.

9. A device according to claim 5, wherein said support frame comprises a umbrella-like shaped reticular arrangement comprising a plurality of radial arms and having centripetally converging ends hinged to a common central hub and opposed ends secured to said peripheral edge.

10. A device according to claim 9, wherein said arms are made of a flexible memorizing material, so as to maintain a memorized original shape, or to take it back after an imposed elastic deformation.

11. A device according to claim 6, wherein said guiding element comprises a telescopic stem so configured to adjust its length in respect of said planar element.

12. A device according to claim 1, further comprising a protective peripheral envelop inside which said vascular device is arranged.

\* \* \* \* \*